United States Patent [19]

Mooring

[11] 4,430,074
[45] Feb. 7, 1984

[54] METHOD FOR THE INTRAVENOUS ADMINISTRATION OF PLURAL SOLUTIONS THROUGH A COMMON FLOW MONITORING STATION

[75] Inventor: William L. Mooring, Dudley, N.C.

[73] Assignee: Samuel Ernest Douglass, Raleigh, N.C.

[21] Appl. No.: 280,089

[22] Filed: Jul. 2, 1981

[51] Int. Cl.³ .......................................... A61M 31/00
[52] U.S. Cl. ........................................ 604/49; 604/93
[58] Field of Search ................. 128/DIG. 13, 214 E, 128/214 G, 214 R; 604/49-54, 290

[56] References Cited

U.S. PATENT DOCUMENTS

| | | | |
|---|---|---|---|
| 3,563,090 | 2/1971 | Deltour | 128/214 E |
| 3,921,630 | 11/1975 | McPhee | 128/214 R |
| 3,941,126 | 3/1976 | Dietrich et al. | 128/214 G |
| 4,105,029 | 8/1978 | Virag | 128/214 G |
| 4,155,362 | 5/1979 | Jess | 604/52 |
| 4,219,912 | 9/1980 | Adams | 128/214 G |
| 4,336,800 | 6/1982 | Pastrone | 604/247 |
| 4,355,639 | 10/1982 | Di Salvo | 604/247 |
| 4,383,252 | 5/1983 | Purcell | 128/DIG. 13 |

Primary Examiner—C. Fred Rosenbaum
Assistant Examiner—J. L. Kruter
Attorney, Agent, or Firm—Mills and Coats

[57] ABSTRACT

The present invention relates to an efficient method of automatically and sequentially intravenously administering two separate solutions to a patient by utilizing a Y-type IV set provided with a single drip chamber monitoring station disposed below from a Y-connecting point. Solution from a first container is directed through a first leg, a Y-connecting point and a single drip chamber monitoring station. A portion of this first solution is operative to engage a check valve interposed within a second leg leading from a second solution container to the Y-connecting point. This engagement causes the check valve to close and prohibits flow of solution from said second container to the Y-connecting point. Once the first solution container has emptied, the check valve is deactivated, and solution from the second container can automatically in sequential fashion move to the Y-connecting point. From the Y-connecting point, solution from the second container is directed to and through the single drip chamber monitoring station. By providing the single drip chamber monitoring station below the Y-connecting point, an intermediate pressure head is formed in both the first and second legs between the respective solution containers and the drip chamber monitoring station. This intermediate pressure head formed by the respective solutions tends to drive and force the respective solutions through the drip chamber monitoring station more efficiently.

1 Claim, 1 Drawing Figure

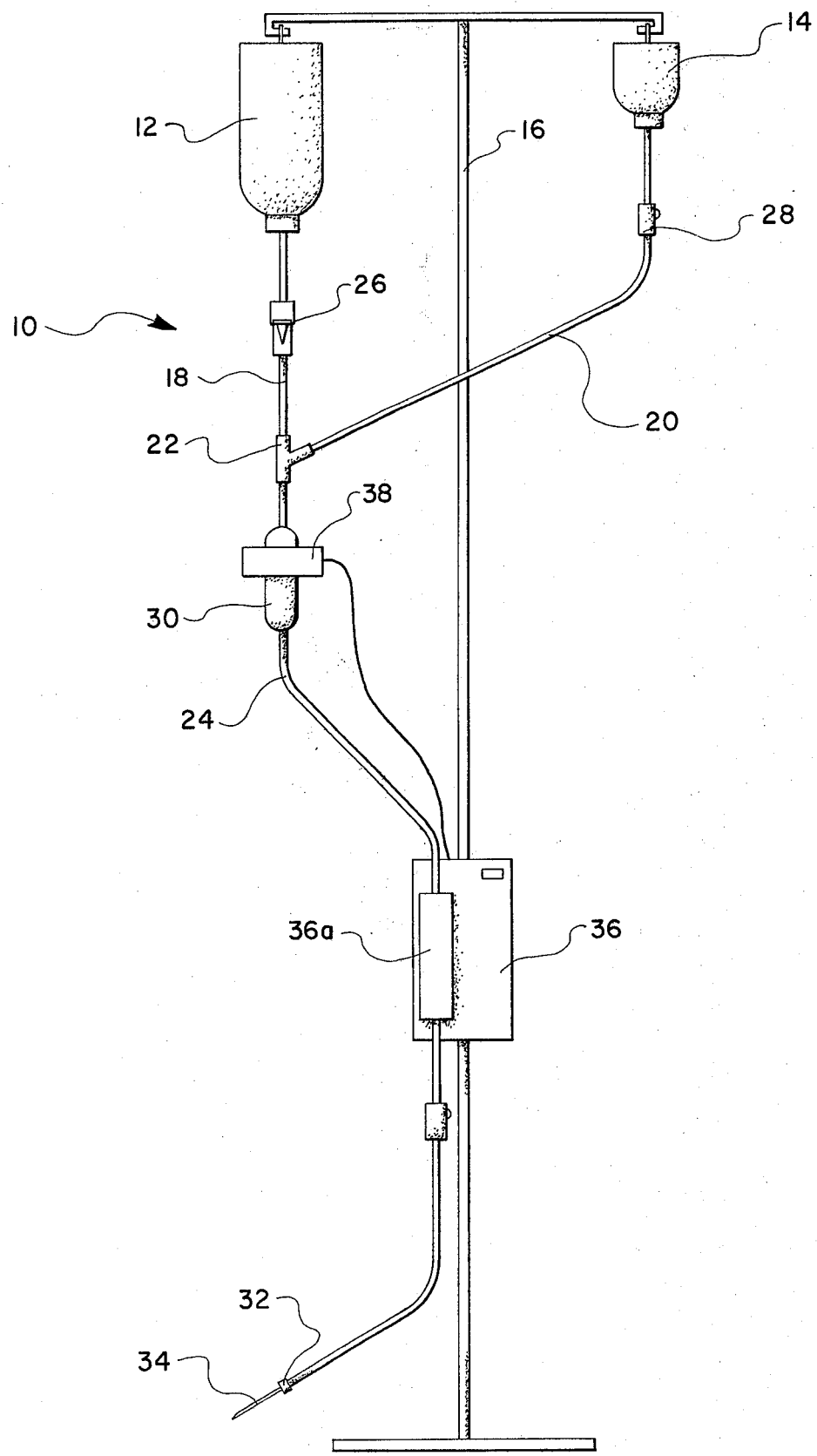

METHOD FOR THE INTRAVENOUS ADMINISTRATION OF PLURAL SOLUTIONS THROUGH A COMMON FLOW MONITORING STATION

FIELD OF INVENTION

The present invention relates to the intravenous administration of a plurality of solutions to a patient through a single venal entry, and more particularly to a Y-type IV set where flow monitoring and control is provided downstream from the Y-connecting point.

BACKGROUND OF INVENTION

For convenience and efficiency, or for purely medical reasons, it is appropriate to administer plural solutions or fluids intravenously to a patient through a single venal entry. Often the fluids or solutions are referred to as primary and secondary solutions, and this process is commonly known in the industry as intravenously piggy-back administration.

Intravenous piggy-back administration is described, for example, in a brochure entitled "New Concepts In Intermittent IV Therapy", published by Travenol Laboratories, Inc., Deerfield, Ill. Typically such a piggy-back IV set will include two upper Y-legs or branches with each line being communicatively connected to either the primary or secondary solution container. The Y-legs will lead from the solution container to a Y-connector. Communicatively connected at the Y-connector is a delivery line that leads therefrom and which is operative to convey the fluid or solution to the patient. A check valve is normally placed in one of the upper Y-legs or lines, typically in the line leading from the primary solution container. The gravitational head of the secondary fluid in the secondary container acts to close the check valve to prevent flow from the primary container. Such a system will deliver the secondary solution to the patient first, and then after the secondary container has been emptied, flow will automatically start from the primary fluid since the check valve automatically opens once the secondary container has emptied.

To monitor and control the administration of both the primary and secondary solutions, there is typically provided a drip chamber between each solution container and the respective upper Y-leg or line. During administration, a drop count controller, typically of the electric eye type, is placed into operative association with the particular drip chamber in the operative line.

Once the first solution container has emptied, and the second container starts to deliver fluid or solution in the other upper Y-leg or line, a nurse or aide must change the drop count controller to another chamber disposed in the other upper Y-leg or line. This obviously requires time on the part of the nurse or aide and actually requires that the total administration process be closely observed and watched in order that proper flow control can be maintained throughout the entire process.

In addition to the time and effort required of the nurse or aide in supervising and managing the intravenous piggy-back administration, the nurse or aide must be careful that air bubbles do not collect and exist beyond either of the respective drip chambers, which essentially involves the entire IV set.

SUMMARY OF INVENTION

The present invention entails a Y-type IV set that is designed to automatically and sequentially intravenously administer two separate solutions by directing both solutions through a common flow monitoring station. More particularly, the present invention entails an IV set including two upper Y-lines or legs that join at a Y-connector or connection point from where there is provided a delivery line for delivering the solution to the patient. Provided within the delivery line, downstream from the Y-connection, is a flow monitoring station such as a drip chamber. In a preferred design of the present invention, there is not provided a flow monitoring station or drip chamber in either of the upper Y-lines. Consequently, flow monitoring and/or control is accomplished exclusively below the Y-connector for all fluid solutions being administered. This enables any one of a plurality of solutions or fluids to be directed from a respective solution container, to the Y-connector and on through the delivery line where the flow is monitored or controlled, without requiring a nurse or aide to shift a drop controller or other control device from one upper Y-line to another after one solution container has emptied.

It is, therefore, an object of the present invention to provide a method and apparatus for intravenously administering two or more solutions that is relatively simple, economical, and minimizes the effort and time required by a nurse or aide in supervising and managing such an administration.

Still another object of the present invention resides in the provision of a piggy-back Y-type IV set that provides a single flow monitoring and/or control station that is capable of monitoring the flow of fluid or solution from any one of a plurality of solution containers.

Another object of the present invention resides in the provision of a Y-type IV set that is provided with a drip chamber below the Y-connector or Y-connection point which enables the flow from any upper Y-line to be monitored by said drip chamber below the Y-connector point.

It is also a further object of the present invention to provide a Y-type piggy-back IV set that is designed to direct a continuous uninterrupted and unmonitored stream of solution from a respective solution container to said Y-connector and therefrom through a drip chamber, wherein the existence of air bubbles in the system is only a problem downstream from the drip chamber.

Other objects and advantages of the present invention will become apparent from a study of the following description and the accompanying drawings which are merely illustrative of the present invention.

BRIEF DESCRIPTION OF DRAWINGS

The FIGURE is a diagrammatic illustration of the Y-type IV set of the present invention shown in conjunction with a drop count controller.

METHOD AND APPARATUS FOR INTRAVENOUSLY ADMINISTERING PLURAL SOLUTIONS

With further reference to the drawings, the Y-type IV set of the present invention is shown therein and indicated generally by the numeral 10. IV set 10 is designed to connect to two solutions, the solutions being referred to herein as a primary solution contained in a primary solution container 12 and a secondary solution contained within container 14. As shown in the drawings, the respective solution containers 12 and 14 are adapted to be supported from a cross member of a rack 16 in conventional fashion.

Turning to the Y-type IV set 10 of the present invention, it is seen that the same includes a pair of feeding lines in the form of a pair of upper legs or branches 18 and 20. Each leg 18 or 20 includes a conventional needle type connector about its upper remote ends that is designed to be inserted into a respective solution container 12 or 14 for directing solution therefrom. Further, legs 18 and 20 lead downwardly where they are communicatively connected by a Y-connector 22. Extending from Y-connector 22 is a delivery leg or branch 24. It is thusly appreciated that upper legs 18 and 20 combine with delivery leg 24 to form the basic Y-type IV set 10.

For purposes of reference, the upper leg connected to the primary solution container 12 is referred to by numeral 18 while the other leg connected to the secondary solution container 14 is referred to by numeral 20. In the embodiment disclosed, upper leg 18 includes a one-way check valve 26 that permits flow from container 12 to Y-connector 22 but which prohibits flow from Y-connector 22 back to solution container 12.

Upper leg 20 includes a thumb clamp 28 that can be utilized to adjust the flow therethrough or even to completely stop the flow.

Provided in delivery leg 24 below Y-connector 22 is a drip chamber 30. It is important to appreciate the position of drip chamber 30 with respect to the Y-type IV set 10 and its components. It is to be appreciated that heretobefore that individual drip chambers were placed in both upper Y-legs 18 and 20 immediately below the solution containers 12 and 14.

Formed about the remote or lower end of delivery leg 24 is a needle adapter 32 that is designed to receive a needle 34 for delivering the particular solution intravenously to a patient.

The Y-type IV set 10 of the present invention is designed to work in conjunction with a conventional drop count controller 36 or other type of flow control devices. As seen in the drawings, there is provided a drop sensor 38 operatively associated with controller 36 that is designed to be secured about drip chamber 30. Moreover, delivery leg 24, in conventional fashion, is threaded through a flow control chamber 36a associated with controller 36. The flow control chamber 36a acts to compress and release said delivery leg 24 in a modulating manner to control the flow therethrough in response to the count of drops passing through drip chamber 30.

Consequently it is appreciated that in the case of the present invention, both primary and secondary solutions can be monitored and/or controlled through a single monitoring station that in the present case comprises the drip chamber 30 and an associated monitoring or control device such as the controller 36. The present Y-type IV set design enables high primary and secondary solutions to be administered sequentially without requiring a nurse or aide to reposition the controller 35 and/or drop sensor 38 between drip chambers disposed in the upper legs 18 or 20.

In carrying out the method of the present invention, the solution to be administered first is suspended at a height above the other solution or solutions. Typically the secondary solution is administered first and accordingly in the case of the present disclosure, the secondary solution container 14 would be elevated above primary solution container 12. The pressure head associated with the elevation of secondary solution container 14 would effectively close check valve 26. The closing of check valve 26 prohibits flow from the primary container 12. While check valve 26 is closed, the secondary solution within container 14 passes through upper leg 20, through Y-connector 22 into delivery leg 24. As the secondary solution passes through delivery leg 24, it is constrained to pass through the flow monitoring station therein comprised of drip chamber 30 and any associated control device. Consequently, the secondary solution is monitored continuously at a point below Y-connector 22.

Once the secondary solution has emptied from container 14, the pressure head acting against check valve 26 no longer exists and, therefore, check valve 26 opens. The opening of check valve 26 allows the primary solution in container 12 to automatically and sequentially begin to flow through upper leg 18 and into the delivery leg 24. As outlined above, the primary solution is monitored by the same monitoring or flow control station as already discussed in conjunction with the secondary solution.

It should be pointed out that the Y-type IV set 10 and the method of the present invention can be utilized with other types of flow control devices. For example, it is contemplated that the present Y-type IV set and method of administration can be carried out with a positive pressure volumetric pump. Here again the important consideration is in the provision of the flow monitoring and/or control station below the Y-connector 22 as contrasted to providing such in the respective upper or feeding legs of the IV set.

From the foregoing specification, it is apparent that the method and apparatus of the present invention presents a novel approach to the intravenous administration of plural solutions by directing the respective solutions through a common flow monitoring and/or control station, thereby negating the requirement of rearranging controls each time one solution has emptied. This design and approach greatly increases the efficiency of plural solutions administration and substantially simplifies the management and supervision of such. In addition, the very nature of the design itself reduces the area of the IV set where the problem with air bubbles is critical since that area is below the drip chamber and because the present design effectively shifts the flow monitoring station or drip chamber to an area much closer to where the respective solution actually enters the patient's body.

The present invention, of course, may be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced herein.

What is claimed is:

1. An efficient method of automatically and sequentially intravenously administering two separate solutions to a patient with a Y-type IV set wherein during administration each solution is monitored by a single drip chamber control station disposed downstream from a Y-connecting point, thereby obviating the necessity of altering or changing the IV set and its control devices during the period in which the two solutions are being administered, said method comprising:

(a) elevating a first solution container containing a first solution above a second solution container containing a second solution;

(b) generating and forming a substantial intermediate pressure head between said solution containers and said monitoring station positioned below said Y-connecting point;

(c) said step of forming said substantial intermediate head pressure between said solution containers and said control station including the step of forming an elongated column of solution in first and second legs leading from said first and second solution containers, respectively, to said Y-connecting point;

(d) directing the first solution from the higher elevated first solution container to the first leg leading from said first solution container;

(e) directing a portion of said first solution into operative engagement with a check valve interposed intermediately within the second leg leading from said second solution container to said Y-connecting point so as to effectively close said check valve and to prevent flow of said second solution from said second solution container to said Y-connecting point;

(f) directing flow of said first solution from said Y-connecting point through the flow control station positioned in a delivery leg leading from said Y-connecting point such that the flow of said first solution is not monitored until the same moves downstream from said Y-connecting point;

(g) utilizing the substantial intermediate head pressure formed in said first leg between said first solution container and said control station to drive and force solution passing from said first solution container through said first leg into said control station;

(h) continuing to direct flow from said first solution container through said first leg and to said Y-connecting point and into said delivery leg where said solution passes through said control station formed therein, and continuing such delivery of said first solution until a selected volume of said first solution has been administered;

(i) deactuating said check valve in said second leg branch, and directing a stream of second solution from said second solution container through said second leg to the Y-connecting point;

(j) utilizing the substantial intermediate head pressure formed in said second leg between said second solution container and said control station to drive and force solution passing from said second solution container through said second leg into said control station; and (k) directing said second solution from said Y-connecting point through said delivery leg and the flow monitoring station therein, wherein the flow of said second solution is monitored subsequently of the Y-connecting point but prior to reaching the patient.

* * * * *